(12) United States Patent
Putz et al.

(10) Patent No.: US 7,536,215 B2
(45) Date of Patent: May 19, 2009

(54) CORTICAL SENSING DEVICE WITH PADS

(75) Inventors: David A. Putz, Pewaukee, WI (US); Alfons Schnellberger, Pfaffstaett (AT)

(73) Assignee: Ad-Tech Medical Instrument Corp., Racine, WI (US)

( * ) Notice: Subject to any disclaimer, the term of this patent is extended or adjusted under 35 U.S.C. 154(b) by 330 days.

(21) Appl. No.: 11/132,488

(22) Filed: May 19, 2005

(65) Prior Publication Data
US 2006/0264729 A1 Nov. 23, 2006

(51) Int. Cl.
*A61B 5/04* (2006.01)
(52) U.S. Cl. .................. 600/378; 600/383; 607/116; 607/139
(58) Field of Classification Search .............. 600/372, 600/375, 377–378, 386, 391
See application file for complete search history.

(56) References Cited

U.S. PATENT DOCUMENTS

| | | | | |
|---|---|---|---|---|
| 4,869,255 | A * | 9/1989 | Putz | 600/378 |
| D404,134 | S * | 1/1999 | Dunshee | D24/189 |
| 6,306,146 | B1 * | 10/2001 | Dinkler | 606/130 |
| 6,624,510 | B1 * | 9/2003 | Chan et al. | 257/734 |
| 7,049,478 | B1 * | 5/2006 | Smith | 602/42 |
| 7,107,097 | B2 * | 9/2006 | Stern et al. | 607/2 |

* cited by examiner

Primary Examiner—Lee S Cohen
(74) Attorney, Agent, or Firm—Jansson Shupe & Munger Ltd.

(57) ABSTRACT

A cortical sensing device is provided that includes a sensing element and at least one pad attached adjacent to a support member. The pad is substantially thin and made from flexibly-conformable material to accurately and safely place the sensing device upon the brain surface. Contact between the lower surface of the pad and the brain surface anchors the sensing element at a desired position against unintentional movement. The sensing device preferably has three circular pads equidistant from one another. A method to position a cortical sensing device upon a brain surface is also disclosed comprising the steps of providing a cortical sensing device having a sensing element and three dielectric pads attached to a support dielectric member where the member and the pads are thin and flexibly-conformable, placing the sensing device upon the brain surface at a desired position for sensing brain activity, and allowing the pads to conform to the brain surface so that interaction therebetween prevents movement of the sensing element along the brain surface.

25 Claims, 4 Drawing Sheets

CORTICAL SENSING DEVICE WITH PADS

FIELD OF THE INVENTION

This invention is related generally to intracranial sensing devices and, more particularly, to cortical sensing devices.

BACKGROUND OF THE INVENTION

Surgical removal of epileptogenic brain is indicated for the treatment of many medically refractory focal seizure disorders. Such surgery demands a high degree of accuracy in identifying the epileptogenic foci. Various methods have been used in attempting to determine the location of these foci, and all involve sensing cortical electrical activity using electrical contacts applied in various ways.

While scalp contacts were customarily used for many years to identify epileptogenic foci, accurate localization of the loci was usually very difficult with the recordings obtained from such contacts. Therefore, many medical centers in recent years have progressed to using intracranial recording techniques to better define regions of cortical epileptogenicity whereby the safety and effectiveness of epileptogenic brain removal is enhanced.

Intracranial recording techniques have typically involved one of two different types of sensing devices—intracortical depth electrodes or cortical strip electrodes. While depth electrodes are necessary in certain circumstances, techniques using cortical strip electrodes have been shown to be relatively safe and serve as valuable alternatives.

The relative safety of cortical strip electrodes lies in the fact that, unlike depth electrodes, they are not invasive of brain tissue. Depth electrodes are narrow, typically cylindrical dielectric structures with contact bands spaced along their lengths. Such electrodes are inserted into the brain in order to establish good electrical contact with different portions within the brain. Cortical strip electrodes, on the other hand, are flat strips that support contacts spaced along their lengths. Such strip electrodes are inserted between the dura and the brain, along the surface of and in contact with the brain, but not within the brain.

A cortical strip electrode has a flexible dielectric strip within which a plurality of spaced aligned flat contacts and their lead wires are enclosed and supported in place between front and back layers of the material forming the dielectric strip. Each flat contact has a face or main contact surface which is exposed by an opening in the front layer of the dielectric strip. Insulated lead wires, one for each contact, are secured within the strip and exit the strip from a proximal end. The dielectric material used in such cortical strip electrodes is typically a flexible, bio-compatible material such as silicone.

While the typical cortical strip electrode works fine in many situations, there are applications for which its structure is not well suited. For instance, monitoring may be desired at a variety of positions around the surface of the brain. The placement of a number of strip electrodes, with their associated multiple contacts, may be more than is necessary. Cortical sensing devices that allow sensing elements such as electrical contacts to be individually positioned at various positions around the brain surface in an easy and safe manner would be an improvement over the current state of the art.

One can appreciate that when a sensing element of a cortical sensing device is placed in contact with the cortex, it is critical that the sensing element remain in that same fixed position relative to the cortex since knowledge of its exact position is necessary to properly interpret the device's readings. The typical cortical electrode is, however, not well anchored or held in place at its desired position upon the brain without being sandwiched between the dura and the cerebral cortex. With these electrodes, it is hoped then that they will not be moved and, for this reason, precautions are often made so as not to disturb the externally positioned lead wires. Nevertheless, movement of the electrode can occur and this movement may even cause inadvertent penetration of the brain. Thus, there is a need for an improved cortical sensing device which can be anchored at a desired position such that it is much less likely to penetrate brain tissue inadvertently and better able to remain at its selected position upon the brain.

OBJECTS OF THE INVENTION

It is an object of the invention to provide an improved cortical sensing device that prevents injury to the patient.

Another object of the invention is to provide a cortical sensing device that is easy to place at a desired position on the brain surface.

Another object of the invention is to provide a cortical sensing device that anchors itself to the brain surface so as to prevent unintentional movement of the sensing device with respect to the brain surface.

Another object of the invention is to provide a cortical sensing device that provides a large surface area contacting the brain.

Another object of the invention to provide a method of accurately positioning a cortical sensing device upon the brain surface.

These and other objects of the invention will be apparent from the following descriptions and from the drawings.

SUMMARY OF THE INVENTION

The invention is for an improved cortical sensing device facilitating the positioning of and maintenance of a sensing element at a desired position on a brain surface. The sensing device includes a support member with a sensing element and at least one pad attached to it. The pad is substantially thin and made from material that is flexibly-conformable. Flexibly-conformable refers to the ability of the pad to easily conform to the contours of the brain surface where the sensing device is placed while being able to recover its original shape and size when removed. The pad is positioned adjacent to the support member. Interaction between the brain surface and the lower surface of the pad contacting the brain surface permits the sensing device to be anchored at the location where it is placed.

In certain preferred embodiments, the pad comprises a single layer of material. More preferred is where the support member is also comprised of a single layer of material. Most desirable is where both the support member and the pad are formed from a unitary layer of material.

A highly preferred embodiment finds abutment between the lower surface of the pad and the brain surface to be substantially complete, i.e., there is little area on the lower surface of the pad not making direct contact with the brain. More desirable is where the support member and the pad are formed from a dielectric, bio-compatible material, most preferably silicone.

Also desirable are embodiments where the sensing device has a plurality of pads and the centers of the support member and each of the pads are not collinear. Highly preferred embodiments find each of these pads attached to the support member along an arc that has a length less than the pad's diameter and less than the diameter of the support member.

This allows each pad to be easily folded along this arc in a manner independent of any of the other pads in a direction generally orthogonal to the surface of the support member.

In another embodiment found preferred, the sensing device has only three pads. In this embodiment, it is highly desirable to have the support member and the pads substantially circular and where each of the pads are attached along the circumference of the support member such that the centers of the pads are equidistant to one another. In this manner, the sensing device is substantially clover-shaped.

Most desirable is where the pad and the support member are each comprised of a single layer of material having a thickness ranging from 0.003 in. to 0.020 in. More preferred is where the thickness is less than 0.010 in. A highly preferred embodiment finds the thickness to be 0.006 in. Certain embodiments have the diameter of the support member and each pad ranging from 0.25 in. to 0.35 in. Most desirable is where the diameter is 0.30 in.

In other embodiments that are preferred, the sensing device has at most one sensing element. In these embodiments, the sensing device desirably also has a lead extending from the sensing element. More preferred is where the sensing element is an electrical contact capable of sensing cortical electrical activity and the lead is a lead wire. Where the sensing element is an optical sensor, the lead is oftentimes a fiber optic bundle. Most desirable embodiments find the lead wire communicating this cortical electrical activity to an external monitor.

A highly desired embodiment is one where the lead wire has a distal socket and this socket is sized to engage a connecting pin on a connector in a frictionally snug manner. The connector has an electrical conduit extending from it to the external monitor and is secured to a support apparatus that preferably includes an adjustable clamp adapted to clamp to the skull during surgery.

Most preferred is where the support apparatus has a post with a mount secured at the distal end and a clamp at the proximal end. The connector in this embodiment is attached to the mount. The clamp has upper and lower clamping portions where the lower clamping portion extends from the proximal end of the post and the upper clamping portion is slidably mounted to the post in registry with the lower clamping portion. The support apparatus also includes an adjustment member that is threadably mounted upon the post between the mount and the upper clamping portion. Adjusting the position of the adjustment member along the post allows it to limit the extent to which the upper clamping portion may slide axially away from the lower clamping portion. Such adjustments also can serve to urge the upper clamping portion in the direction of the lower clamping portion.

Another aspect of this invention finds a method for positioning a cortical sensing device on the surface of the brain. The method has the steps of (1) providing an sensing device having a sensing element supported by a dielectric member and three dielectric pads attached to this support dielectric member where the support member and the pads are each substantially thin and flexibly-conformable; (2) placing this sensing device upon the brain surface at a desired position for sensing brain activity; and (3) allowing the pads to conform to the brain surface whereby interaction between the pads and the brain surface prevents movement of the sensing device along the brain surface.

In a preferred embodiment, the method also includes the step of bathing the sensing device in a solution of saline or sterile water. Highly preferred is where the sensing device includes a lead extending from the sensing element for communicating brain activity sensed by the sensing element to an external monitor. Most desirable is where the sensing element is an electrical contact capable of sensing cortical electrical activity and the lead is a lead wire.

DETAILED DESCRIPTION OF PREFERRED EMBODIMENTS

Figure 1:
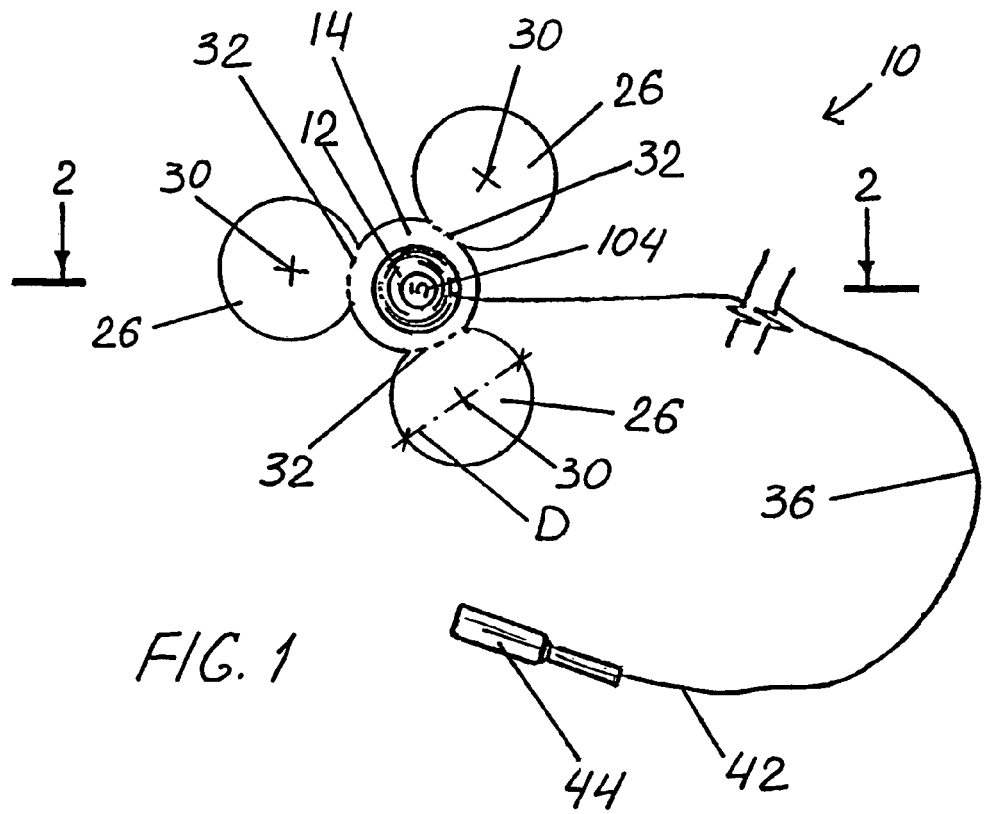
FIG. 1 is a top view of a preferred cortical sensing device in accordance with this invention.

FIG. 1 is a top view of a cortical sensing device 10 having a preferred embodiment in accordance with this invention. Cortical sensing device 10 includes a sensing element, preferably an electrical contact 12 as shown, secured to circular support member 14. Support member 14 is provided with a circular opening 16 surrounded by a rim 18. Contact 12 has a central disk 20 with support-flange 22 extending along the circumference of disk 20. Opening 16 is sized to receive disk 20 in a manner where lower surface 24 of disk 20 can protrude downward from and not be covered by support member 14. Disk 20 protrudes no more than 0.025 in. through opening 16 and, in certain preferred embodiments, lower surface 24 is flush with support member 14. Support-flange 22 is preferably adhesively sealed along its length to rim 18.

Cortical sensing device 10 is also provided with three substantially similar circular pads 26 extending outward from support member 14. Support member 14 and pads 26 are formed from a single thin and substantially planar layer 28 of a dielectric material that is both flexible and bio-compatible. A silicone material such as a medical grade of SILASTIC® is preferred although an equivalent dielectric elastomer can also be used. The material is also preferably transparent to enable the underlying features of the cortical surface to be visualized when sensing device 10 is placed upon the brain.

Figure 2:
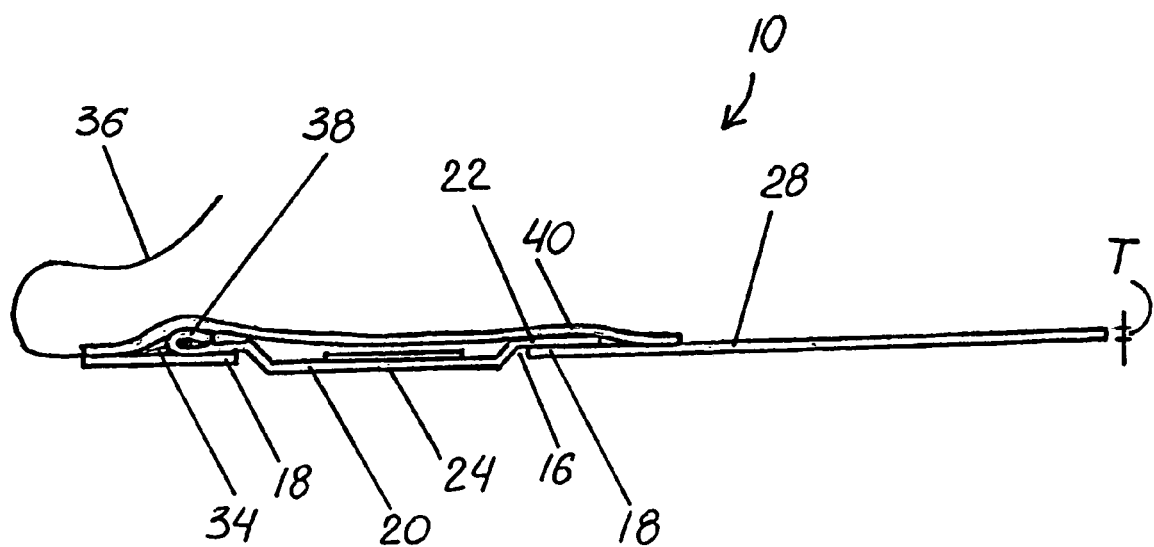
FIG. 2 is a cross-sectional view of the cortical sensing device taken substantially along line 2-2 of FIG. 1.

As illustrated in FIGS. 1-2, layer 28 has a thickness T and each pad 26 has a diameter D. The thickness of layer 28 is substantially uniform throughout the strip, preferably about 0.006 in. The diameter of each pad 26 ranges from 0.25 in. to 0.35 in. The center 30 of each pad 26 is equidistant from the centers of the other two pads, thereby forming a clover-like shape. Each pad 26 is attached to support member 14 along an arc 32.

A proximal end 34 of a single lead wire 36 is electrically secured to contact 12 by solder or by being crimped within lip 38 of support-flange 22. As seen in FIG. 2, upper cover 40 is placed over contact 12 and adhesively sealed to support member 14. Cover 40 is formed from a transparent, bio-compatible, dielectric material similar to that comprising layer 28. Cover 40 has a diameter slightly less than that of support member 14. A portion of wire 36 is embedded between cover 40 and support member 14 to further firmly secure wire 36 to sensing device 10. Distal end 42 of wire 36 is electronically attached to socket 44.

Figure 3:
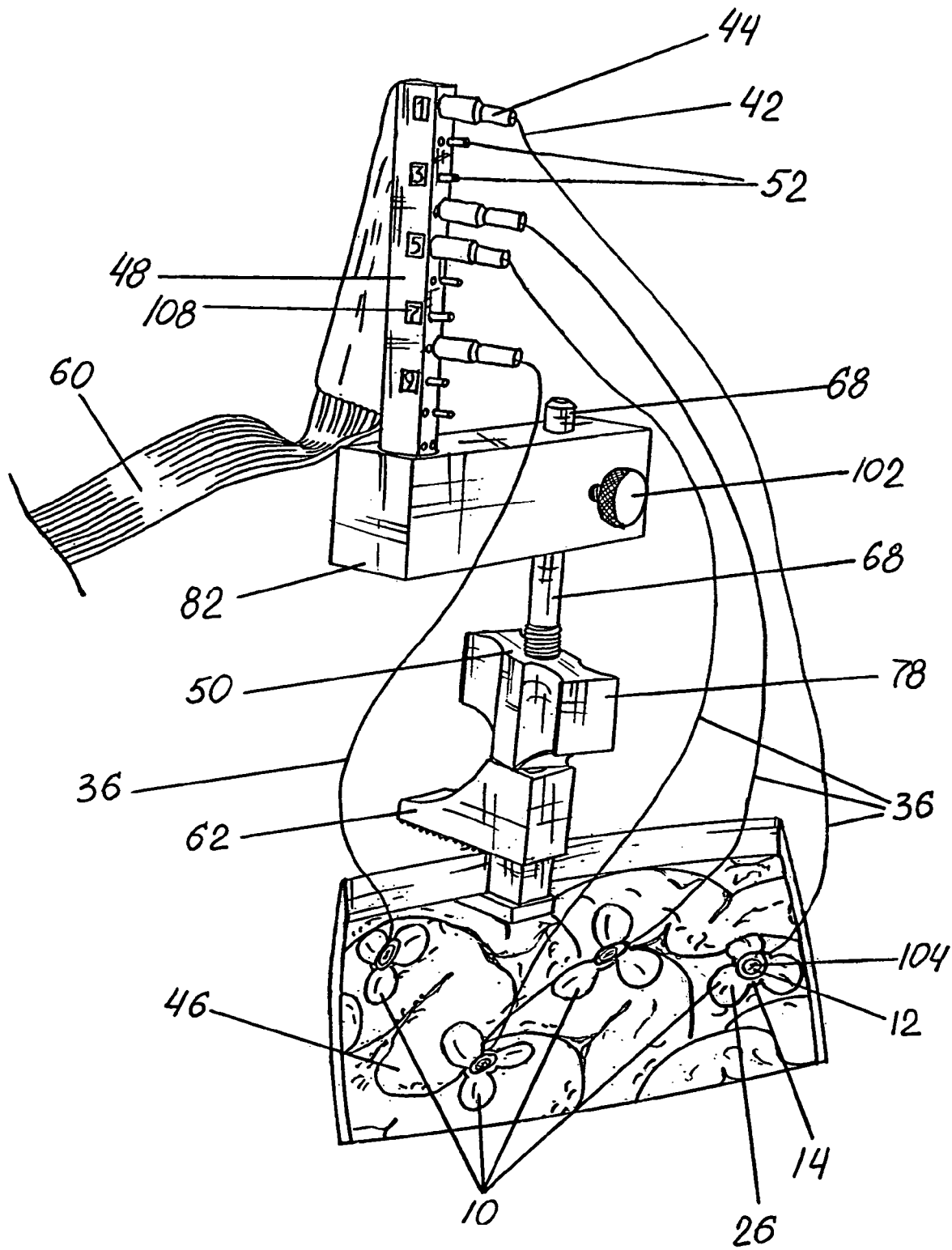
FIG. 3 is a perspective view of several of the cortical sensing devices in FIG. 1 shown in contact with the brain surface and attached to a connector and support apparatus in accordance with this invention.

FIG. 3 shows a number of sensing devices 10 positioned upon the surface 46 of the cerebral cortex following a craniotomy. Sockets 44 of each wire 36 have a tapered interior to snugly receive a connector pin 52 on a connector 48 in frictional engagement. Connector 48 is mounted upon a support apparatus 50, each being illustrated in FIGS. 3-5 in a preferred embodiment in accordance with this invention.

Pads 26 interact with brain surface 46 so that sensing device 10 clings to the cortex. Lateral movement of sensing device 10 is avoided once each sensing device 10 has been individually positioned at a desired specific location that is selected by the physician for that sensing device 10 to perform a certain procedure such as sensing brain activity. Bathing each sensing device 10 in saline or sterile water before placing it upon brain surface 46 helps in preparing sensing device 10 for secure placement.

Disk surface 24 of contact 12 makes direct contact with brain surface 46. Contact 12 is preferably platinum or stainless steel and can be utilized to measure brain electrical activity or to provide electrical stimulation to a select tissue region. Other sensing elements such as chemical sensors and optical sensors can be used in place of or in connection with an electrical contact or electrode to monitor chemical activity, temperature and blood flow within the cortex. Pulling upward upon sensing device 10 in a direction away from brain surface 46 allows sensing device 10 to be disengaged from brain surface 46 for relocation to another site on brain surface 46 where sensing device 10 can initiate similar treatment.

As can be seen in FIG. 3, pads 26 do not need to be sandwiched between the dura and the cortex to remain in place. Moreover, given the size and shape of sensing device 10, one can clearly see that the weight of sensing device 10 is less of a factor in its ability to stay in one spot than is the case for the heavier strip sensing devices in the prior art.

The thinness of pads 26, the length of arcs 32, and the nature of the material selected for layer 28 each contribute to the ability of pads 26 to retain their shape but still be sufficiently flexible to conform to an area of brain surface 46 of comparable size. Each arc 32 has a length less than the diameter of support member 14 and less than the diameter of pad 26. Each pad 26 is capable of swinging about its adjacent arc 32 independently of any other pad 26 such that each pad 26 is free to drape over the portion of brain surface 46 directly beneath it. In this manner, sensing device 10 provides as much as 300% more area in direct contact with brain surface 46 than is touched by contact 12 and its surrounding support member 14 alone.

Figure 4:
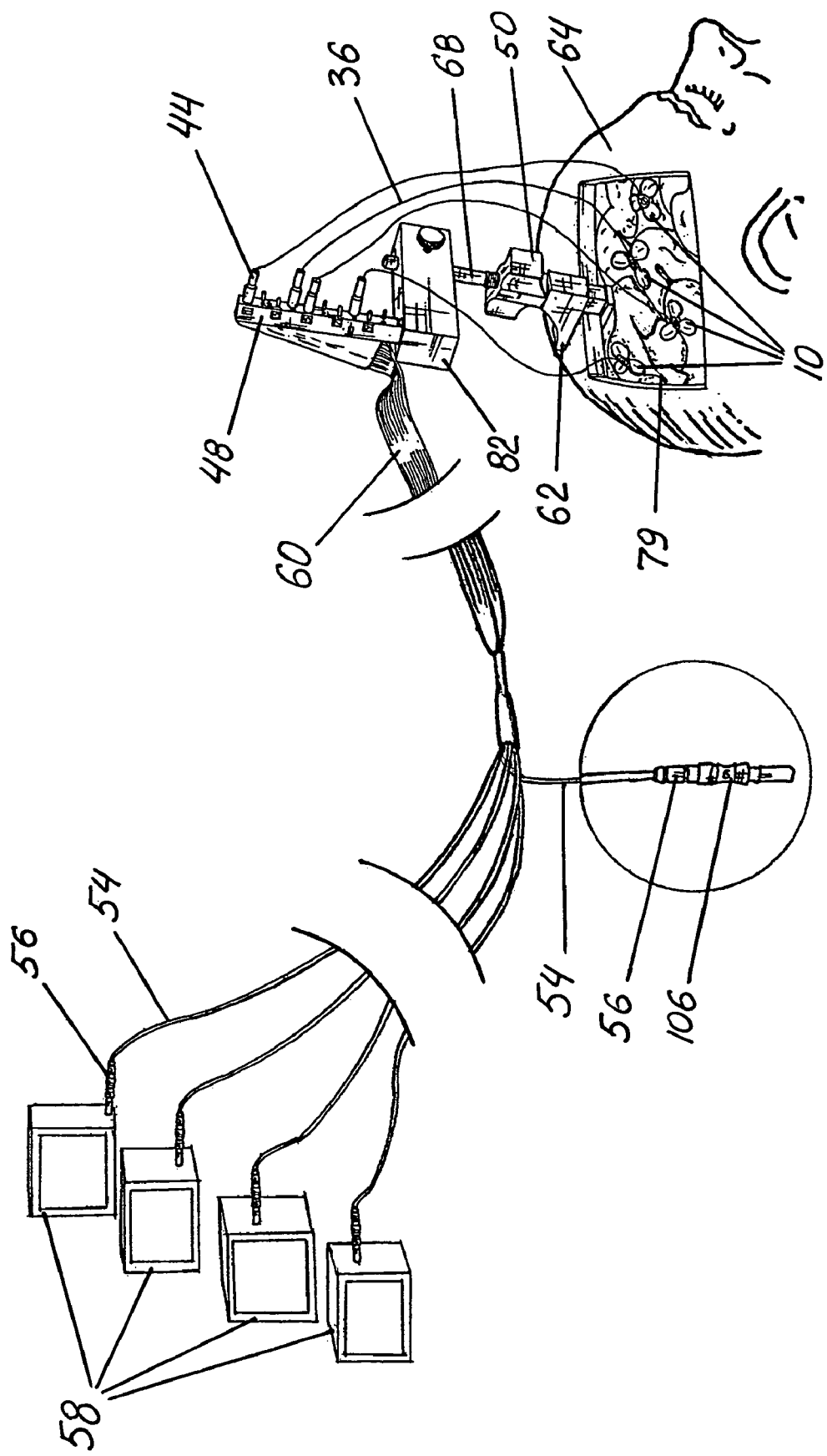
FIG. 4 is a schematic view illustrating the connection of the cortical sensing devices of FIG. 3 to external devices through the connector and electrical conduit in accordance with this invention and with an enlarged view of an input jack on the electrical conduit.
Figure 5:
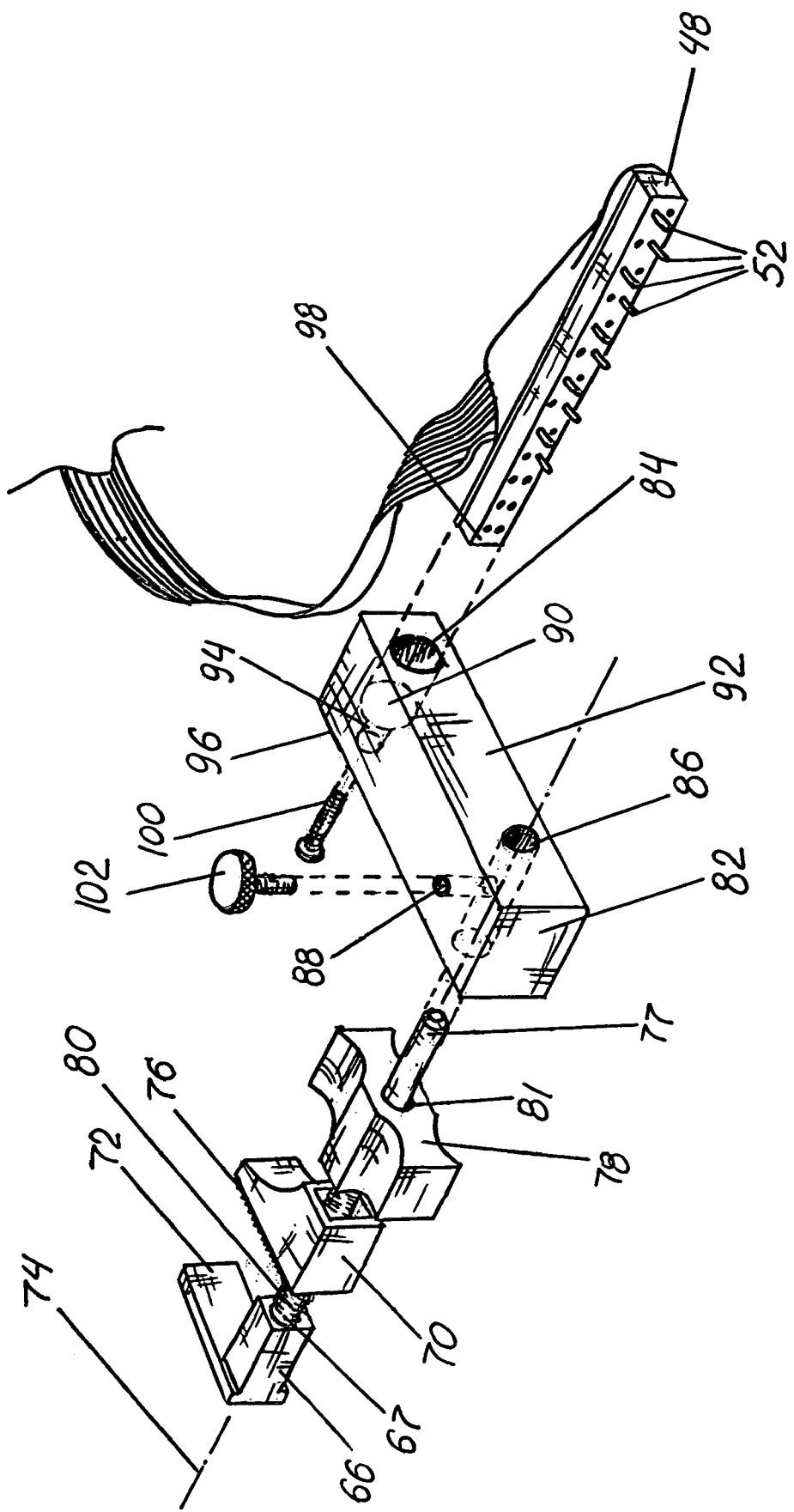
FIG. 5 is an exploded view of the support apparatus in FIG. 3 with the connector disengaged from the mount.

As illustrated in FIGS. 3-5, connector 48 is provided with a plurality of connecting pins 52. Each pin 52 is in electrical communication with an electrical conduit 54, each wire conduit 54 having an input jack 56 attached at the end opposite from the corresponding connecting pin 52.

Input jack 56 enables the electrical conduit 54 and thereby the associated sensing device 10 to be connected to an external device 58. Where sensing device 10 is intended to monitor electrical brain activity, external device 58 will preferably consist of a conventional monitoring device with output display and a suitable power source to record or display information communicated by sensing device 10. Electrical conduits 54 preferably combine to form a conduit ribbon 60 upon exiting connector 48 so that individual loose wires can be avoided. As seen in FIG. 4, conduit ribbon 60 separates into the individual electrical conduits 54 at a distance from connector 48 to enable one or more input jacks 56 to be electronically attached to the necessary external devices 58.

Connector 48 is mounted to support apparatus 50 to provide better access to connector 48 during treatment of a patient. As illustrated in FIGS. 3 and 4, support apparatus 50 includes a clamp 62 for attaching support apparatus 50 to the skull 64. Clamp 62 comprises a lower clamping portion 66 forming the proximal end 67 of a post 68 and an upper clamping portion 70 slidably disposed upon post 68. FIG. 5 shows that lower clamping portion 66 has a smooth lower clamping surface 72 extending outward from axis 74 of post 68. Upper clamping portion 70 is provide with a serrated upper clamping surface 76 that is in registry with lower clamping surface 72.

In mounting support apparatus 50 to the skull 64, the spacing between both clamping surfaces 72,76 is increased by sliding upper clamping portion 70 in the direction of the distal end 77 of post 68. Lower clamping portion 66 is inserted into an opening 79 in skull 64 so that lower clamping surface 72 can be placed up against the interior surface of skull 64. Upper clamping portion 70 is then lowered to bring upper clamping surface 76 in contact with the exterior surface of skull 64.

Support apparatus 50 includes adjustment member 78 to stop upper clamping portion 70 from sliding upward and to maintain upper and lower clamping portions 66,70 firmly in contact with skull 64. Adjustment member 78 has a threaded bore 81 that is threadably mounted upon post 68 along a threaded portion 80 adjacent to lower clamping portion 66. Adjustment member 78 can then be rotated in a conventional manner so that adjustment member 78 is forcefully urged against upper clamping portion 70 to reduce the spacing between clamping portions 66,70 and thereby firmly tighten clamp 62 upon skull 64.

Support apparatus 50 also includes mount 82. As seen in FIG. 5, mount 82 is provided with three apertures 84,86,88. First aperture 84 is at one end of mount 82 and has a top portion 90 opening onto top surface 92 and a bottom portion 94 opening onto bottom surface 96. Portions 90,94 are coaxial but have different diameters. Top portion 90 is sized to receive the bottom end 98 of connector 48 so that connector 48 can then be secured to mount 82 by having a fastener 100, preferably a screw, threadably engage bottom end 98 through bottom portion 94.

Second aperture 86 is at the other end of mount 82 and extends from top surface 92 to bottom surface 96. Second aperture is adapted to receive the distal end 77 of post 68. Third aperture 88 is orthogonal to and in communication with second aperture 86. Third aperture 88 is sized to threadably receive a grip screw 102. Post 68 is firmly secured within mount 82 by threadably advancing grip screw 102 within third aperture 88 until grip screw 102 is urged into contact with and frictionally engages post 68. One can readily see that mount 82 can be raised or lowered along post 68 or pivoted about post 68 before grip screw 102 is tightened so that a desirable position for mount 82 in relation to skull 64 and thereby the adjacent surgical field can be achieved.

As shown in FIG. 4, each input jack 56 is numbered, preferably with a collar 106 embedded with numerical indicia. Likewise, a numerical decal 108 is fastened on the connector 48 adjacent to each connecting pin 52. The number on the collar 106 of each input jack 56 is the same number found on the decal 108 corresponding to the connecting pin 52 that is connected via electrical conduit 54 to that specific input jack 56. One can appreciate that in this manner the physician or technician can immediately identify which sensing device 10 is being monitored by a specific external device 58 by matching the number on the collar 106 of the input jack 56 connected to that device with the corresponding number on the connector 48 to see which sensing device 10 is engaged to the connecting pin 52 associated with that number. In a similar fashion, the connecting pin 52 associated with a certain desired external device 58 can be easily identified when attaching sensing devices 10 to connector 48 or when replacing one sensing device 10 with another such as when a lead breaks or contact 12 becomes inoperative.

Sensing devices 10 are also provided with numerical indicia 104 to use to distinguish one sensing device from the others. Although the physician or technician remains free to attach the socket 44 for a given sensing device 10 to any empty or unattached connecting pin 52 on the connector 48, connecting the socket 44 to the connecting pin 52 having a number on the adjacent decal 108 that matches the number on the sensing device 10 itself will permit that individual to more quickly, easily and with greater assurance associate each sensing device 10 with a corresponding external device 58.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A conical sensing device comprising:
   a support member having a lower surface and a center;
   a sensing element secured with respect to the support member at the center; and
   at least three substantially thin pads, the pads being spaced apart from each other and being individually integrally attached to the support member, each pad consisting of a single unitary layer of flexibly-conformable material having a center, a uniform thinness, and a lower surface, each pad being sufficiently thin to allow the lower surface to cling to a brain surface such that direct conformance alone between the lower surface and the brain surface anchors the sensing element at one of a plurality of desired positions, the lower surfaces of the pads together having a greater surface area than the lower surface of the support member, and the centers of the support member and pads not being collinear.

2. The sensing device of claim 1 wherein the support member is comprised of a single layer of material.

3. The sensing device of claim 2 wherein the support member and the pads are formed from a unitary layer of material.

4. The sensing device of claim 1 wherein direct conformance between the lower surface and the brain surface is substantially complete.

5. The sensing device of claim 4 wherein the support member and the pads are formed from a dielectric, bio-compatible material.

6. The sensing device of claim 5 wherein the support member and the pads are silicone.

7. The sensing device of claim 1 wherein the support member and each pad has a diameter and each pad is attached to the support member along an arc, the arc having a length less than the diameter of both the support member and the adjacent pad, whereby each pad can be folded along the adjacent arc independently of any other pad.

8. The sensing device of claim 7 wherein the sensing device has only three pads.

9. The sensing device of claim 8 wherein the support member and the pads are substantially circular and have circumferences, the pads being attached along the circumference of the support member such that the centers of the pads are equidistant to one another.

10. The sensing device of claim 1 wherein the pads and the support member are each comprised of a single layer of material, the material having a thickness ranging from 0.003 in. to 0.020 in.

11. The sensing device of claim 10 wherein the thickness is less than 0.010 in.

12. The sensing device of claim 11 wherein the thickness is 0.006 in.

13. The sensing device of claim 1 wherein the diameter of the support member and each pad ranges from 0.25 in. to 0.35 in.

14. The sensing device of claim 13 wherein the diameter is 0.30 in.

15. The sensing device of claim 1 wherein the sensing device has at most one sensing element secured to the support member.

16. The sensing device of claim 15 further comprising a lead extending from the sensing element.

17. The sensing device of claim 16 wherein the sensing element is an electrical contact for sensing cortical electrical activity and the lead is a lead wire.

18. The sensing device of claim 17 further comprising an external monitor and wherein the lead wire communicates cortical electrical activity to the external monitor.

19. The sensing device of claim 18 further comprising a support apparatus having a connector secured with respect thereto, the connector having an electrical conduit extending to the external monitor, and wherein the lead wire has a socket, the socket being sized to snugly engage a connecting pin on the connector.

20. The sensing device of claim 19 wherein the support apparatus further includes an adjustable clamp adapted to receive a skull, whereby the apparatus can be clamped to the skull during surgery.

21. The sensing device of claim 20 wherein the support apparatus further includes:
   a post having an axis and proximal and distal ends;
   a mount having the connector secured with respect thereto and being secured with respect to the distal end;
   the clamp having upper and lower clamping portions, the lower clamping portion extending from the proximal end and the upper clamping portion being slidably mounted with respect to the post in registry with the lower clamping portion; and
   an adjustment member threadably mounted with respect to the post between the mount and the upper clamping portion, whereby the upper clamping portion is limited from sliding axially towards the proximal end by the adjustment member.

22. A method of positioning a cortical sensing device on a brain surface comprising:
   providing a cortical sensing device having a support dielectric member, the member having a lower surface and a center and the member supporting a sensing element at the center, and three dielectric pads, the pads being spaced apart from each other and being individually integrally attached to the support dielectric member, the member and the pads being substantially thin and flexibly-conformable, each pad consisting of a single unitary layer of uniform thinness having a lower surface, each pad being sufficiently thin to allow the lower surface to cling to the brain surface, the lower surfaces of the pads together have a greater surface area than the lower surface of the support member, and each pad having a center wherein the centers of the member and the pads are not collinear;
   placing the sensing device upon the brain surface such that the sensing element is at one of a plurality of desired positions for sensing brain activity; and allowing the pads to conform to the brain surface whereby direct conformance alone therebetween prevents movement of the sensing device along the brain surface.

23. The method of claim 22 further comprising bathing the sensing device in a solution wherein the solution is saline or sterile water.

24. The method of claim 22 wherein the sensing element senses brain activity and the sensing device includes a lead extending from the sensing element for communicating brain activity to an external monitor.

25. The method of claim 24 wherein the sensing element is an electrical contact for sensing cortical electrical activity and the lead is a lead wire.

* * * * *